(12) United States Patent
Paufique

(10) Patent No.: US 9,463,149 B2
(45) Date of Patent: Oct. 11, 2016

(54) **USE OF AN ACTIVE PRINCIPLE DERIVED FROM *EUCHEUMA COTTONII* AND RICH IN LINEAR GALACTANS FOR CONTROLLING SKIN CELL AGING**

(71) Applicant: SOCIETE INDUSTRIELLE LIMOUSINE D'APPLICATION BIOLOGIQUE, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 0 days.

(21) Appl. No.: 14/375,455

(22) PCT Filed: Feb. 6, 2013

(86) PCT No.: PCT/FR2013/050251
§ 371 (c)(1),
(2) Date: Jul. 30, 2014

(87) PCT Pub. No.: WO2013/117859
PCT Pub. Date: Aug. 15, 2013

(65) Prior Publication Data
US 2015/0025036 A1   Jan. 22, 2015

(30) Foreign Application Priority Data
Feb. 6, 2012   (FR) ..................... 12 51087

(51) Int. Cl.
A61K 8/73   (2006.01)
A61K 8/97   (2006.01)
A61Q 19/08  (2006.01)

(52) U.S. Cl.
CPC . *A61K 8/73* (2013.01); *A61K 8/97* (2013.01); *A61Q 19/08* (2013.01)

(58) Field of Classification Search
CPC ........... A61K 8/73; A61K 8/97; A61Q 19/08

USPC ........................................... 514/54
See application file for complete search history.

(56) References Cited

U.S. PATENT DOCUMENTS 4,443,486 A   4/1984   Guiseley

FOREIGN PATENT DOCUMENTS

| FR | 2 480 138   | 10/1981    |
|----|-------------|------------|
| FR | 2 719 846   | 11/1995    |
| FR | 2719846     | * 11/1995  |
| JP | 2002 193736 | 7/2002     |
| WO | WO8404039   | * 10/1984  |
| WO | 2009/114749 | 9/2009     |

OTHER PUBLICATIONS

Glossary of medical education terms, Institute of International Medical Education. http://www.iime.org/glossary.htm Accessed in Mar. 2013.*
Matsui et al.Sulfated Polysaccharides from Red Microalgae Have Antiinflammatory Properties In Vitro and In Vivo. Applied Biochem Biotechnol 104: 13-22, 2003.*
Stortz et al. Specific fragmentation of carrageenans. Carbohydrate Res 166:317-323, 1987.*
Jol et al. A Novel High-Performance Anion-Exchange Chromatographic Method for the Analysis of Carrageenans and Agars Containing 3,6-Anhydrogalactose. Analytical Biochemistry 268,:213-222, 1999.*
International Search Report dated Jan. 21, 2014, corresponding to PCT/FR2013/050251.

* cited by examiner

*Primary Examiner* — Clinton Brooks
*Assistant Examiner* — Yih-Horng Shiao
(74) *Attorney, Agent, or Firm* — Young & Thompson

(57) ABSTRACT

A cosmetic active principle produced by the hydrolysis of *Eucheuma cottonii* and including linear galactans, as well as to the use thereof for promoting the protection of the telosome and telomeres of skin cells and thereby preventing and/or controlling skin aging. Also, the cosmetic compositions including the active principle and a cosmetic skincare method.

15 Claims, No Drawings

USE OF AN ACTIVE PRINCIPLE DERIVED FROM EUCHEUMA COTTONII AND RICH IN LINEAR GALACTANS FOR CONTROLLING SKIN CELL AGING

This invention relates to the use of an active ingredient derived from *Eucheuma cottonii* and rich in specific molecules for combating the aging of the skin and enhancing the perceived age, as well as to a particular active ingredient containing such molecules.

The invention also relates to the cosmetic compositions including this active ingredient and a cosmetic treatment method intended to prevent and/or to combat skin aging.

One of the first visible consequences of human aging is the change in skin parameters characterized by the appearance of wrinkles and loosening of the skin.

At the cellular level, aging, known as senescence, is an irreversible state in which the damaged cells no longer proliferate.

Senescence can occur on two major paths: premature senescence induced by stress and replicative senescence. The latter is inherent in cell division and marks the decline of the replicative potential of the fibroblasts. The cells are in effect provided with a division quota that decides their lifespan. When this quota is exhausted, the fibroblasts cease their proliferation and enter into senescence, a normal physiological process that prevents the transformation of the cell.

Replicative senescence is dependent on telomeres, DNA sequences that are noncoding and highly repeated located at the ends of the chromosomes, and protected by a specific protein complex, the telosome. In the course of cell divisions, the telomeres gradually grow shorter up to a critical minimum size that triggers the cellular senescence state, contributing to the degeneration of the skin tissue and to its aging.

The objective of this invention is to propose a cosmetic active ingredient that facilitates the protection of the telosome and of the telomeres of the skin cells, to maintain the cellular replicative potential, and to enhance the perceived age.

For this purpose, the object of the invention is the use of particular molecules obtained from *Eucheuma cottonii*.

*Eucheuma cottonii* is a branched, red seaweed, green to orangey-yellow in color, cultivated primarily in Asia, particularly in the Pacific area for the production of gelling agents and thickeners, used in the food, pharmaceutical and cosmetic sectors. For example, the application FR2480138, which describes a sulfated extract of *Eucheuma cottonii* as a viscous food additive, can be cited.

Moreover, extracts have been used in cosmetics for hydrating, emulsifying, emollient, smoothing, gelling or else slimming properties. In particular, the application FR2719846 that mentions the use of sulfated galactans that exhibit a sulfation rate of at least 0.5 sulfate per saccharide unit to improve the elasticity of the skin and to facilitate healing is known. These sulfated galactanes can be carrageenans obtained from *Eucheuma* sp. by a process involving fermentation by marine bacteria. The application JP2002193736 that describes aqueous extracts of *Eucheuma cottonii* for the smoothing of skin and of hair is also known.

The object of this invention is specifically the use of an active ingredient obtained by hydrolysis of *Eucheuma cottonii* containing linear galactans as a cosmetic active ingredient in a composition for skin application, said active ingredient and/or said composition being intended to facilitate the protection of the telosome and of the telomeres in the cells of the skin. The active ingredient contains very few, if any, sulfated galactans.

Actually, surprisingly enough, the cosmetic use of an ingredient obtained by hydrolysis of *Eucheuma cottonii* containing linear galactans facilitates the protection of the telosome and of the telomeres in the fibroblasts and thus makes it possible to maintain the cellular replicative potential for a visible anti-aging effect.

Specifically, the invention also relates to a particular active ingredient, namely a hydrolysate of *Eucheuma cottonii* comprising linear galactans, intended to be incorporated into a skin application composition.

"Skin application composition" is defined as any composition intended to be applied on the skin, preferably a cosmetic composition.

"Hydrolysate" is defined as any extract obtained from *Eucheuma cottonii*, comprising at least one hydrolysis step.

Finally, the invention also has as its object a cosmetic composition containing an active ingredient obtained from *Eucheuma cottonii* containing linear galactans, as well as a cosmetic treatment method intended to prevent and/or to combat the effects of age on the skin, comprising the topical application on the skin of such a composition.

This invention is now described in detail.

Use

According to a first aspect, the object of the invention is a hydrolysate of *Eucheuma cottonii* comprising linear galactans, for its use as a cosmetic active ingredient in a skin application composition, said active ingredient and/or said composition being intended to facilitate the protection of the telosome and telomeres of the cells of the skin.

The telomeres guarantee the integrity of the chromosomes. They protect, on the one hand, the ends of the chromosomes to keep them from degrading, and they prevent, on the other hand, the loss of genetic information during replication. However, these chromosome ends are fragile and are themselves stabilized by a multi-protein complex called telosome or shelterin.

The telosome plays a very important role of protection while making it possible for the telomeres to adopt a particular lasso shape, called a telomere loop. It hides the telomeres and keeps them from degrading while nevertheless allowing their access at regular intervals to make it possible for them to replicate.

The telosome is composed of 6 central proteins, including POT1 ("Protection Of Telomeres") and TPP1 ("POT1 and TIN2-interacting protein," proteins interacting with POT1 and TIN2). These proteins of the telosome actively participate in the protection of the telomeres, and the applicant has demonstrated in particular that their expressions are significantly reduced in senescent fibroblasts compared to normal fibroblasts.

When the telosomes are altered or in the absence of a telosome, the weakened telomeres grow shorter more quickly with each division. Stress (UV, radicals reactive to oxygen, etc.) also accentuates their wear and tear.

The alteration of the telomeres, resulting at the same time from their gradual erosion and/or their unmasking via a failure of the telosome, controls the stopping of the proliferation and leads to cellular senescence, called replicative or telomere senescence. This process brings about, via different mechanisms, a gradual decline of the functionality of the skin tissue and its aging.

According to the invention, the use on the skin of an active ingredient obtained from *Eucheuma cottonii* comprising linear galactans makes it possible to limit the losses at the level of the telomeres of the fibroblasts. In particular, an active ingredient obtained from *Eucheuma cottonii* comprising linear galactans can be used to:

preserve the capacity of the fibroblasts to express POT1 and TPP1, proteins of the telosome whose expressions are reduced in senescent fibroblasts, and limit the shortening of the telomeres in the fibroblasts, in particular to prevent the accelerated erosion of the telomeres caused by stress.

By limiting the losses at the level of the telomeres, at each cellular division, the active ingredient according to the invention makes it possible to preserve the replicative capital of the fibroblasts and to delay the phenomena of senescence and degeneration.

Cellular longevity is facilitated, the passage of the human fibroblasts into cellular senescence is limited, and the appearance of the signs of aging is slowed. An active ingredient obtained from *Eucheuma cottonii* comprising linear galactans can therefore be used to prevent and/or to combat the appearance of the signs of aging on the skin and to enhance the perceived age. It makes it possible, in particular:

to facilitate the restructuring of the dermal matrix, and to smooth the skin microrelief by reducing the roughness of the skin and by attenuating wrinkles.

In particular, it can be used specifically to prevent and/or to combat the appearance of wrinkles.

According to a particularly suitable embodiment, the object of the invention is the use in a composition of an active ingredient obtained from *Eucheuma cottonii*, as described below.

Active Ingredient

The invention also relates to a particular cosmetic active ingredient, namely a hydrolysate of *Eucheuma cottonii* comprising linear galactans. The degree of polymerization of the linear galactans is preferably between 6 and 18. The useful linear galactans according to the invention are not sulfated linear galactans: less than 1% of the linear galactans present in the hydrolysate according to the invention are sulfated.

The active ingredient preferably exhibits a clear yellow color.

It appears in the form of a non-viscous liquid product. It can be defined by at least one of the characteristics mentioned below, preferably all.

Dry Materials:

The level of dry materials of an active ingredient according to the invention (measured by the passing of a sample of given initial weight through an oven at 105° C. in the presence of sand until a constant weight is obtained) can be between 30 and 100 g/l, preferably between 47 and 65 g/l.

Measurement of the pH:

The pH (measured by the potentiometric method at ambient temperature) can be between 3 and 5, preferably between 3 and 4.

Carbohydrates:

Determination of the Content of Total Sugars

The metering of the content of total sugars can be performed by the DUBOIS method (M. DUBOIS et al., (1956), Analytical Chemistry, 28, No. 3, pp. 350-356). In the presence of concentrated sulfuric acid and phenol, the reducing sugars yield an orangey-yellow compound. From a standard range, the level of total sugars of a sample can be determined.

The content of total sugars can be greater than 45% by weight of dry material, preferably greater than 60%.

Preferably, the content of total sugars is between 19 and 71 g/l, in particular between 31 and 46 g/l.

Characterization of the Carbohydrate Fraction:

The determination of the size of the carbohydrates of an active ingredient according to the invention is performed by high-performance liquid chromatography.

The chromatogram that is obtained shows the presence of monosaccharides with a molecular mass of less than 180 Da and of oligosaccharides and of polysaccharides with a molar mass of between 180 and 8,100 Da (degree of polymerization at most 45). The monosaccharides represent less than 35%, preferably between 18 and 25%, and the oligosaccharides and polysaccharides with a molar mass of between 180 and 8,100 Da represent at least 65%, preferably between 72 and 85%.

The glucidic fraction of the active ingredient according to the invention is therefore composed essentially of monosaccharides, oligosaccharides and polysaccharides with a degree of polymerization of less than 45.

The majority of the carbohydrates present in the active ingredient are linear galactans.

Level of Sulfated Carbohydrates:

The level of sulfated carbohydrates in aqueous matrices is determined with a spectrophotometry method.

The sulfated carbohydrates yield a blue coloring in the presence of azure A.

The level of sulfated carbohydrates in the samples is determined relative to a standard range achieved with a sulfated dextran solution of known concentration.

Less than 1% of the carbohydrates of the active ingredient according to the invention are sulfated carbohydrates.

Content of Raw Ash:

The content of raw ash is determined by weighing the residues obtained from incineration at 550° C. in an electric muffle furnace (VULCAN™).

The weight of the residue is calculated by subtracting the tare.

The mineral content is expressed in terms of percentage relative to the total weight of the dry material of the active ingredient.

The raw ash content of an active ingredient according to the invention is preferably less than 30%.

Content of Uronic Acids:

The product of galacturonic acid with sodium tetraborate yields, in the presence of meta-hydroxydiphenyl, a pink coloring making possible spectrophotometer metering at 520 nm.

The intensity of coloring is proportional to the amount of uronic acids. The readings are performed from a standard range of galacturonic acid that goes from 10 to 100 mg/l.

The samples of the active ingredient according to the invention must first be diluted with distilled water.

The results obtained for the standards make it possible to draw a straight line DO=f(concentration).

The level of uronic acids of the products is then directly read on this straight line.

The content of uronic acids of an active ingredient according to the invention is preferably less than 25%.

Production Method

The active ingredient according to the invention as described above can be obtained preferably by a method comprising hydrolysis.

A particularly suitable method comprises at least the series of the following steps:

solubilization of *Eucheuma cottonii* powder in aqueous solution, hydrolysis of carbohydrates, separation of soluble and insoluble phases to recover the soluble phase, filtering and recovery of the filtrate, concentration of the active fraction containing linear galactans.

Preferably, the method comprises at least the series of the following steps:

solubilization of *Eucheuma cottonii* powder in aqueous solution, hydrolysis of carbohydrates, separation of soluble and insoluble phases to recover the soluble phase, filtering and recovery of the filtrate, concentration of the active fraction containing linear galactans, filtering, sterilizing filtering.

Steps for deodorizing and color removal can be added.

The parameters of the various steps must be adjusted so as to obtain active ingredients comprising linear galactans, preferably linear galactans with a degree of polymerization mainly between 6 and 18.

The production method according to the invention, in particular the hydrolysis of the carbohydrates that is performed, is performed to make it possible to eliminate the sulfated carbohydrates naturally present in the seaweed.

Cosmetic Compositions and Cosmetic Skin Care Method

This invention also covers the cosmetic compositions that include linear galactans obtained from *Eucheuma cottonii* or a *Eucheuma cottonii* hydrolysate comprising linear galactans, in various galenic formulations, suitable for administration by cutaneous topical means.

These compositions can appear in particular in the form of oil-in-water emulsions, water-in-oil emulsions, multiple emulsions (water/oil/water or oil/water/oil) that can optionally be microemulsions or nanoemulsions, or in the form of solutions, suspensions, aqueous dispersions, aqueous gels or powders. They can be more or less fluid and have the appearance of a cream, a lotion, a milk, a serum, an ointment, a gel, a paste or a mousse, or be in solid form.

They can be compositions comprising between 0.01 and 3% of ingredient(s) obtained from *Eucheuma cottonii* comprising linear galactans according to this invention.

These compositions comprise, in addition to the active agent, a medium that is physiologically acceptable and preferably cosmetically acceptable, that is to say that does not cause unacceptable sensations of discomfort for the user such as redness, tingling, or prickling.

The compositions according to the invention can contain as an adjuvant at least one compound selected from among:

oils, which can be selected in particular from among the linear or cyclic, volatile or non-volatile silicone oils;

waxes, such as ozokerite, polyethylene wax, beeswax or carnauba wax;

silicone elastomers;

surfactants, preferably emulsifiers, whether they are non-ionic, anionic, cationic or amphoteric;

co-surfactants, such as linear fatty alcohols;

thickeners and/or gelling agents;

moisturizers, such as polyols like glycerin;

organic filters;

inorganic filters;

dyes, preservatives, feedstocks;

tightening agents;

sequestering agents;

perfumes;

and their mixtures, without this list being limiting.

Examples of such adjuvants are cited in particular in the CTFA Dictionary (International Cosmetic Ingredient Dictionary and Handbook published by the Personal Care Product Council).

Of course, a person skilled in the art will be sure to select the optional complementary compounds, active or inactive, and their amount, so that the advantageous properties of the mixture are not, or are approximately not, altered by the envisaged addition.

These compositions are in particular intended to facilitate the protection of the telosome and telomeres, in particular to prevent and/or to combat the effects of aging on the skin.

For this purpose, the object of the invention is a cosmetic method for care of human skin, intended to prevent and/or to combat the effects of aging on the skin, in particular by facilitating the protection of the telosome and the telomeres, comprising the topical application of a composition containing non-sulfated linear galactans obtained from *Eucheuma cottonii* or an *Eucheuma cottonii* hydrolysate that comprises linear galactans according to this invention.

EXAMPLES

A nonlimiting example of a method for producing an active ingredient obtained from *Eucheuma cottonii* containing linear galactans is presented as follows, as well as composition examples that include such an active ingredient.

Example 1

Method of Producing the Active Ingredient According to the Invention

An example of a method of producing an active ingredient according to the invention comprises the implementation of the following steps:

solubilization of 50 g/l of *Eucheuma cottonii* powder in aqueous solution, hydrolysis of carbohydrates in an acid medium, separation of soluble and insoluble phases, and recovery of the soluble phase, filtering of the soluble phase and recovery of the filtrate containing the linear galactans with an average degree of polymerization of less than 45, concentration of this active fraction, filtering, sterilizing filtering.

The active ingredient that is obtained has the following characteristics:

appearance: clear liquid color: clear yellow content of dry materials: 52.7 g/l pH: 3.6 content of total sugars: 38.7 g/l, or 73.5% by weight in relation to the dry material, of which 78% is in the form of linear galactans content of sulfated carbohydrates: 0.22 g/l, or less than 1% of the carbohydrates of the active ingredient ash content: 17.1% content of uronic acids: 9.4%

Example 2

Use of an Active Ingredient According to the Invention in a Night Cream

| Phase A. | Water | Enough to produce 100% |
|---|---|---|
| | Glycerol | 4.9% |
| Phase B. | Cire de Lanol ™ CTO (Seppic) | 6% |
| | DUB RG AE (Stéarinerie DUBOIS) | 4.2% |
| | Montanov 202 (Seppic) | 4% |
| | Montanov 68 (Seppic) | 4% |
| | DUB Vinyl (Stéarinerie DUBOIS) | 1.4% |
| | DUB PTIS (Stéarinerie DUBOIS) | 2% |
| | Lanol 2681 (Seppic) | 2% |
| Phase C. | DC 73 101 (Dow Corning) | 5.4% |
| | Silicone Microcare M1600 (Thor) | 4% |
| Phase D. | Active ingredient according to the invention (Example 1) | 3% |
| | Preservative | 0.7% |

The amounts indicated are given as a percentage of weight.

This thick, melting, white silicone emulsion has a pH of 6.8. In topical application on the skin, it has a rapid penetration with a smooth finish.

It can be obtained by implementing the following steps:
mixing A, heating in a boiling-water bath to 80° C. while being stirred mechanically,
mixing B, heating in a boiling-water bath to 80° C. while being stirred mechanically,
emulsifying B in A with a rotor-stator at 1,100 rpm,
mixing C, heating in a boiling-water bath to 50° C., and adding C to the emulsion when it reaches 60° C., with a rotor-stator at 1,200 rpm,
adding D, at 30° C., in the order indicated, with a rotor-stator at 1,500 rpm, and
leaving it to cool while regularly lowering the stirring speed of the rotor-stator, until the emulsion is completely homogenized.

Example 3

Use of an Active Ingredient According to the Invention in a Day Cream

| Phase A. | Water | Enough to produce 100% |
|---|---|---|
| | Carbopol Ultrez 20 (Noveon) | 0.2% |
| Phase B. | Ritaphyl ICS (Rita) | 2% |
| | DUB Vinyl (Stéarinerie DUBOIS) | 1.4% |
| | Cetearyl Alcohol | 2% |
| | DUB BA (Stéarinerie DUBOIS) | 1.4% |
| | Pelemol 2014 (Phoenix Chemical) | 2% |
| Phase C. | Preservative | 0.7% |
| | Active ingredient according to the invention (Example 1) | 3% |
| Phase D. | NaOH | Enough to produce pH 6 |

The amounts indicated are given as a percentage of weight.

This creamy, white emulsified gel has a pH of 6. In topical application, it has a velvety application with a smooth finish and a powdered effect.

It can be obtained by implementing the following steps:
mixing A, heating in a boiling-water bath to 80° C. while being stirred mechanically, and while ensuring good dispersion of the gel,
mixing B, heating in a boiling-water bath to 80° C. while being stirred mechanically,
emulsifying B in A with a rotor-stator at 3,600 rpm,
adding C, at 40° C., in the order indicated, with a rotor-stator at 3,000 rpm,
leaving it to cool,
adjusting the pH with D, at 30° C., while being stirred mechanically at 1,800 rpm and leaving it to stir until the emulsified gel is completely homogenized.

Example 4

Use of an Active Ingredient According to the Invention in a Liquid Cleanser

| Phase A. | Water | Enough to produce 100% |
|---|---|---|
| | Glycerol | 3.7% |
| | Satialgine US551 (Degussa) | 0.7% |
| Phase B. | Montanov 68 (Seppic) | 2.5% |
| | Pelemol BB (Phoenix Chemical) | 2.7% |
| | Pelemol 2014 (Phoenix Chemical) | 3.7% |
| | Montanov S (Seppic) | 3% |
| | Sophiderm (Sophim) | 3.4% |
| | DUB MCT 5545 (Stéarinerie Dubois) | 3.2% |
| | DUB OK 18 (Stéarinerie Dubois) | 4% |
| | DUB IPP (Stéarinerie Dubois) | 4% |
| Phase C. | Preservative | 0.7% |
| | Active ingredient according to the invention (Example 1) | 3% |

The amounts indicated are given as a percentage of weight.

This white, liquid emulsion has a pH of 6.8. It is easily emulsified in water, in the form of a smooth and fine mousse, with a dry finish.

It can be obtained by implementing the following steps:
mixing A, dispersing the gel in a boiling-water bath to 80° C. while being stirred mechanically at 1,000 rpm,
mixing B, heating in a boiling-water bath to 80° C. while being stirred magnetically,
emulsifying B in A with a rotor-stator at 1,800 rpm,
heating A to 60° C. while being stirred mechanically at 1,000 rpm,
leaving it to stir until cooling is complete.

Example 5

Use of an Active Ingredient According to the Invention in an Anti-Wrinkle Serum

| Phase A. | Water | Enough to produce 100% |
|---|---|---|
| | Glycerol | 3% |
| | Blanose 7M31CF (Hercules) | 1% |
| Phase B. | DUB 1632 (Stéarinerie Dubois) | 6.9% |
| | DUB PTCC (Stéarinerie Dubois) | 3% |
| | Refined palm oil (Sictia) | 2.7% |
| | DUB 340 (Stéarinerie Dubois) | 2.7% |
| | DC 9040 (Dow Corning) | 3.7% |
| | Rita GMS (Rita) | 2% |
| | Montanov 14 (Seppic) | 1.7% |
| Phase C. | Preservative | 0.7% |
| | Active ingredient according to the invention (Example 1) | 3% |

The amounts indicated are given as a percentage of weight.

This white, liquid emulsion gel has a pH of 5.5. In topical application, it has a comfortable spreading with a slightly film-forming, cottony finish.

It can be obtained by implementing the following steps:
- mixing A, heating in a boiling-water bath to 80° C. while being stirred mechanically, and while ensuring good dispersion of the gel (about 800 rpm),
- mixing B, heating in a boiling-water bath to 80° C. while being stirred magnetically,
- emulsifying B in A with a rotor-stator at 1,100 rpm,
- adding C, immediately in the order indicated, with a rotor-stator at 3,000 rpm,
- leaving it to cool, while being stirred, until homogenization is complete.

Example 6

Use of an Active Ingredient According to the Invention in an Anti-Wrinkle Emulsion

| Phase A. | Water | Enough to produce 100% |
|---|---|---|
| Phase B. | Lanol 99 (SEPPIC) | 5% |
| | Montanov 202 (SEPPIC) | 3% |
| | Montanov 68 (SEPPIC) | 2% |
| Phase C. | Preservative | 0.7% |
| Phase D. | Sepigel 305 (SEPPIC) | 0.3% |
| Phase E. | Active ingredient according to the invention (Example 1) | 3% |

The amounts indicated are given as a percentage of weight.

This white, liquid emulsion has a pH of 6.8.

It can be obtained by implementing the following steps:
- mixing A, heating in a boiling-water bath to 80° C. while being stirred mechanically, and while ensuring good dispersion of the emulsion (about 800 rpm),
- mixing B, heating in a boiling-water bath to 80° C. while being stirred magnetically,
- emulsifying A in B with a rotor-stator between 2,000 and 5,000 rpm,
- at 50° C., adding C and then D still with a rotor-stator,
- adding E, at 30° C., homogenizing until cooling is complete.

Evaluation of the Cosmetic Effectiveness of an Active Ingredient According to the Invention A. In Vitro Tests I. Study of the Effect on the Protection of the Telomeres—Study of the Expression of the Molecules of the POT1 and TPP1 Telosome The first object of the study is to evaluate the expression of the two major proteins of the telosome that are responsible for the protection of the POT1 telomeres ("Protection of Telomeres") and TPP1 telomeres ("PTO1 and TIN2-interacting protein," protein interacting with PTO1 and TIN2) in senescent human fibroblasts obtained following a moderate and repeated attack with hydrogen peroxide ($H_2O_2$) in comparison with normal human fibroblasts.

The second object of the study is to evaluate the ability of an active ingredient obtained from *Eucheuma cottonii* comprising linear galactans to limit the expression of PTO1 and TPP1 of normal human fibroblasts attacked by the same treatment with hydrogen peroxide.

The study was performed by quantitative PCR on human fibroblasts.

The operating procedure is described below.

On D0, the normal human fibroblasts are seeded in the complete medium.

The cells are then incubated at 37° C.

On D1, D2, D3 and D4, the fibroblasts are processed:

Controls that are not attacked: the normal fibroblasts are processed in the complete medium for 2 hours, in the presence or absence of the active ingredient of Example 1 with 0.25% (V/V), and at the end of the incubation, the culture medium is eliminated and replaced by the medium containing, or not containing, the active ingredient of Example 1 with 0.25% (V/V).

Control that is attacked: the normal fibroblasts are attacked in the complete medium with an $H_2O_2$ solution for 2 hours. The attack, repeated 4 times (D1, D2, D3 and D4), makes it possible to induce the cellular senescent state. These are therefore senescent fibroblasts.

Fibroblasts that are attacked and processed: the normal human fibroblasts are attacked and processed in the complete culture medium with a solution of $H_2O_2$ for 2 hours in the presence or absence of the active ingredient according to Example 1 with 0.25% and 0.50%. At the end of the incubation, the culture medium is eliminated and replaced by the medium containing, or not containing, the active ingredient of Example 1 with 0.25% and 0.50% (V/V).

On D4, the cells are recovered and the total RNA extracted. The RNAs are reverse transcripts, and the complementary DNA that is obtained is analyzed by quantitative PCR (quantitative Polymerase Chain Reaction).

The quantification of the incorporation of fluorescence is continuously measured using a thermal cycler, and the relative quantification is carried out using a software package.

The results obtained for the POT1 protein are presented in the table below:

| | Expression of POT1 (%) | Ability to limit the loss of expression of POT1 (%) |
|---|---|---|
| Control that is not attacked, not processed - Normal fibroblasts | 100 | / |
| Control that is not attacked and processed - Normal fibroblasts processed with the active ingredient according to the invention, 0.25% | 96 | / |
| Control that is attacked, not processed - Senescent fibroblasts | 68 | 0 |
| Fibroblasts that are attacked and processed Active ingredient according to the invention, 0.25% | 90 | +69 |
| Fibroblasts that are attacked and processed Active ingredient according to the invention, 0.50% | 100 | +100 |

The results obtained for the TPP1 protein are presented in the table below:

| | Expression of TTP1 (%) | Ability to limit the loss of expression of TPP1 (%) |
|---|---|---|
| Control that is not attacked, not processed - Normal fibroblasts | 100 | / |

-continued

| | Expression of TTP1 (%) | Ability to limit the loss of expression of TPP1 (%) |
|---|---|---|
| Control that is not attacked and processed - Normal fibroblasts processed with the active ingredient according to the invention, 0.25% | 89 | / |
| Control that is attacked, not processed - Senescent fibroblasts | 82 | 0 |
| Fibroblasts that are attacked and processed Active ingredient according to the invention, 0.25% | 89 | +39 |
| Fibroblasts that are attacked and processed Active ingredient according to the invention, 0.50% | 98 | +89 |

These results show that the expressions of the proteins of the POT1 and TPP1 telosome are significantly reduced on the senescent human fibroblasts relative to those of normal human fibroblasts.

Moreover, it is found that an active ingredient obtained from *Eucheuma cottonii* comprising linear galactans makes it possible to limit the alteration of the expressions of POT1 and TPP1, essential proteins of the telosome.

It prevents the accelerated erosion of telomeres, caused by stress, and checks the premature passing of the fibroblasts into senescence.

In particular tested at 0.5%, the active ingredient of Example 1 makes it possible to limit by 100% the alteration of the expression of POT1 and by 89% the alteration of the expression of TPP1.

II. Study of the Effect on the Length of the Telomeres

This second study has as its object to evaluate the ability of an active ingredient containing linear galactans obtained from *Eucheuma cottonii* to limit the acceleration of the erosion of the telomeres caused by repeated stress.

The study was performed by flow cytometry on pre-senescent human fibroblasts obtained following a moderate and repeated treatment with hydrogen peroxide ($H_2O_2$) according to the operating procedure described below.

On D0, the normal human fibroblasts are seeded in the complete medium. The cells are then incubated at 37° C.

On D1, D2, D3 and D4, the fibroblasts are processed:

Controls that are not attacked: the normal fibroblasts are processed in the complete medium for 2 hours, in the presence or absence of the active ingredient of Example 1 with 0.25% (V/V), and at the end of the incubation, the culture medium is eliminated and replaced by the medium containing, or not containing, the active ingredient of Example 1 with 0.25% (V/V).

Control that is attacked: the normal fibroblasts are attacked in the complete medium with an $H_2O_2$ solution for 2 hours. The attack, repeated 4 times (D1, D2, D3 and D4), makes it possible to induce the cellular senescent state. These are therefore senescent fibroblasts.

Fibroblasts that are attacked and processed: the normal human fibroblasts are attacked and processed in the complete culture medium with an $H_2O_2$ solution for 2 hours in the presence or absence of the active ingredient according to Example 1 with 0.25% and 0.50%. At the end of the incubation, the culture medium is eliminated and replaced by the medium containing, or not containing, the active ingredient of Example 1 with 0.25% and 0.50% (V/V).

On D7, the length of the telomeres is quantified using a dedicated kit.

The results obtained are presented below:

| | Relative length of the telomeres (%) | Ability to limit the shortening of the telomeres (%) |
|---|---|---|
| Control that is not attacked, not processed - Normal fibroblasts | 17.3 | / |
| Control that is not attacked and processed - Normal fibroblasts processed with the active ingredient according to the invention, 0.25% | 16.3 | / |
| Control that is attacked, not processed - Senescent fibroblasts | 15 | 0 |
| Fibroblasts that are attacked and processed Active ingredient according to the invention, 0.25% | 15.6 | +26 |
| Fibroblasts that are attacked and processed Active ingredient according to the invention, 0.50% | 16.5 | +65 |

These results make it possible, during a first step, to show that the shortening of the telomeres is accelerated on senescent fibroblasts relative to normal fibroblasts.

In addition, they show that an active ingredient obtained from *Eucheuma cottonii* comprising linear galactans makes it possible to limit the alteration of the shortening of the telomeres caused by stress. In particular, tested at 0.5%, the active ingredient of Example 1 makes it possible to reduce by 65% the acceleration of the shortening of the telomeres caused by stress.

III. Study of the Effect on the Maintenance of the Cellular Replicative Potential The objective of this study is to evaluate the increase in the activity of the β-galactosidase, a marker of the premature passing of cells into senescence, in senescent human fibroblasts relative to normal human fibroblasts.

It also makes it possible to evaluate the ability of an active ingredient obtained from *Eucheuma cottonii* containing linear galactans to preserve the replicative potential of the cells by limiting their passing into senescence.

The study was performed by coloring of the β-galactosidase on human fibroblasts.

The operating procedure of the study is described below.

On D0, the normal human fibroblasts are seeded in the complete medium. The cells are then incubated at 37° C.

On D1, D2, D3 and D4, the fibroblasts are processed:

Controls that are not attacked: the normal fibroblasts are processed in the complete medium for 2 hours, in the presence or absence of the active ingredient of Example 1 with 0.25% (V/V), and at the end of the incubation, the culture medium is eliminated and replaced by the medium containing, or not containing, the active ingredient of Example 1 with 0.25% (V/V).

Control that is attacked: the normal fibroblasts are attacked in the complete medium with an $H_2O_2$ solution for 2 hours. The attack, repeated 4 times (D1, D2, D3 and D4), makes it possible to induce the cellular senescent state. These are therefore senescent fibroblasts.

Fibroblasts that are attacked and processed: the normal human fibroblasts are attacked and processed in the complete culture medium with an $H_2O_2$ solution for 2 hours in the presence or absence of the active ingredient according to Example 1 with 0.25% and 0.50%. At the end of the incubation, the culture medium is eliminated and replaced by the medium containing, or not containing, the active ingredient of Example 1 with 0.25% and 0.50% (V/V).

On D7, the β-galactosidase activity is viewed using a dedicated kit. The viewing of the activity of the β-galactosidase is performed on a microscope connected to an image analysis system. The activity of the β-galactosidase is proportional to the dark blue coloring. A quantitative analysis of the images is also performed using a software package.

The results obtained are presented below:

|  | β-Galactosidase activity ($10^3$ × A.U.) | Ability to limit the passing into senescence (%) |
|---|---|---|
| Control that is not attacked, not processed - Normal fibroblasts | 40 | / |
| Control that is not attacked and processed - Normal fibroblasts processed with the active ingredient according to the invention, 0.25% | 49 | / |
| Control that is attacked, not processed - Senescent fibroblasts | 317 | 0 |
| Fibroblasts that are attacked and processed Active ingredient according to the invention, 0.25% | 180 | +49 |
| Fibroblasts that are attacked and processed Active ingredient according to the invention, 0.50% | 144 | +62 |

These results show that the activity of the β-galactosidase is increased on human fibroblasts passing into senescence.

It is also found that an active ingredient obtained from *Eucheuma cottonii* containing linear galactans tested at 0.5% makes it possible to limit the premature passing of the fibroblasts into senescence by 62% and thus to preserve their replicative potential.

B. In Vivo Tests

IV. Study of the Effect on the Dermal Matrix

It is known that with age, fundamental changes in the extracellular matrix occur that lead to a deterioration of the collagen network, which is reflected by a disorganization of fibers, a coarser structure, and a reduction in the density of the collagen.

This study has as its object to evaluate in vivo the ability of an active ingredient obtained from *Eucheuma cottonii* containing linear galactans, formulated at 3% in emulsion, to facilitate the restructuring of the dermal matrix that is disrupted with age. The study was carried out versus placebo in the area of the cheeks on two groups of healthy female volunteers:
   one group treated with a placebo emulsion: 21 volunteers with a median age of 59 years
   one group treated with the composition of Example 6 comprising the active ingredient of Example 1 in 3% emulsion: 24 volunteers with a median age of 59 years.

The acquisition measurements of the network of fibers in the area of the cheeks were made from sections, using a confocal microscope, equipped with 3 laser diodes. For the observation of the papillary dermis and the evaluation of collagen fibers, the wavelength of 785 nm was selected.

The visual analysis of the images was carried out using a scoring scale comprising 4 stages by a trained panel. During its evaluation, the panel takes into account both the appearance of the dermal matrix in general and that of the fibers. When the dermal matrix is not altered, the fibers appear in the form of glistening and elongated fibrillar structures arranged in the manner of a spider web. The observation of an aged skin or of photoexposed areas conversely show a matrix composed of thick fibers, coarsely arranged, curled up and fragmented, exhibiting a spongy appearance.

The following scale illustrates the classification used by the panel:

|  | Appearance of the matrix | | Appearance of the fibers | |
|---|---|---|---|---|
|  | Spiderweb network | Coarse and spongy network | Elongated fibers | Fragmented fibers |
| Stage 4 | ++ | − | ++ | − |
| Stage 3 | + | +/− | + | +/− |
| Stage 2 | +/− | + | +/− | + |
| Stage 1 | − | ++ | − | ++ |

The operating procedure of the study is described below.

Between D14 and D0, the volunteers apply a placebo cream on the face twice daily.

On D0, the volunteers do not apply any cream or make-up on the face, and acquisitions by confocal microscopy are carried out in the area of the cheeks.

Between D0 and D41, the placebo or the emulsion containing the active ingredient of Example 1 at 3% is applied twice daily.

On D42, the volunteers do not apply any cream or make-up on the face, and acquisitions by confocal microscopy are again carried out in the area of the cheeks.

The average of the results obtained is presented in the table below:

|  | Stage (A.U.) | | |
|---|---|---|---|
|  | D0 | D42 | Variation/D0 (%) |
| Placebo | 2 | 2 | −0.3 |
| Active ingredient of Example 1 | 2 | 3 | +30.2 |

It is found that under the conditions of this study, after 42 days of twice-daily applications of an active ingredient obtained from *Eucheuma cottonii* comprising linear galactans and compared to the placebo group, the evaluation carried out on a grading scale by an expert panel has shown a significant improvement in the appearance of the dermal matrix by 30.6%.

V. Study of the Anti-Wrinkle Effect

The appearance of wrinkles is one of the first visible signs of skin aging that can be, at least in part, due to the shortening of the length of the telomeres linked to age. Actually, the length of the telomeres can be used as an indicator of the replicative potential of cells and thus be associated with aging.

The objective of the study is to evaluate in vivo the anti-wrinkle effect of an active ingredient obtained from *Eucheuma cottonii* comprising linear galactans formulated at 3% in emulsion versus placebo in the area of crow's feet by fringe projection.

The study was performed versus placebo in the area of the cheeks on two groups of healthy female volunteers:
   a group treated with a placebo emulsion: 21 volunteers with a median age of 59 years
   a group treated with the active ingredient of Example 1 in a 3% emulsion (composition of Example 6): 24 volunteers with a median age of 59 years.

The acquisitions in the area of the crow's feet were carried out using a fringe-projection apparatus dedicated to 3D measurement of the skin relief. This system comprises a measurement sensor combining a light-fringe projector and a high-resolution CCD camera connected to an acquisition software package.

The relevant parameters retained for the study are:
roughness parameters in 3D:
 Sq: quadratic average of surface roughness
 Sa: arithmetic average of surface roughness
a volume parameter:
 negative volume: volume below the surface of the skin A reduction of these different parameters is characteristic of an improvement of the relief of the surface studied and of a reduction of wrinkles.

The operating procedure of the study is described below.

Between D-14 and D0, the volunteers apply a placebo cream on the face twice daily.

On D0, the volunteers do not apply any cream or make-up on the face, and 3D acquisitions onto crow's feet by fringe projection are carried out.

Between D0 and D41, the placebo or the emulsion containing 3% of the active ingredient of Example 1 is applied twice daily.

On D42, the volunteers do not apply any cream or make-up on the face, and 3D acquisitions onto crow's feet by fringe projection are again carried out.

The average of the results obtained with the active ingredient according to the invention is presented in the table below by percentage of variation compared to the results obtained with the placebo:

|  | Variation/Placebo (%) |
| --- | --- |
| Sa Parameter | −8.9 |
| Sq Parameter | −11.0 |
| Negative volume | −27.9 |

It is found that, under the conditions of this study, after 42 days of twice-daily applications and compared to the placebo, an active ingredient obtained from *Eucheuma cottonii* comprising linear galactans makes it possible:
 to smooth the skin relief in the area of the crow's feet (reduction of the Sa and Sq parameters), and
 to reduce the wrinkles (reduction of the negative volume parameter).

In particular, the active ingredient of Example 1 formulated at 3% in emulsion, compared to the placebo, makes it possible to reduce by 8.9% the Sa parameter, by 11.0% the Sq parameter, and by 27.9% the negative volume parameter.

These different studies clearly show that the use on the skin of an active ingredient obtained from *Eucheuma cottonii* comprising linear galactans is capable of facilitating the protection of the telosome and of the telomeres of the cells of the skin and thus makes it possible to prevent and/or to combat the signs of the aging of the skin, such as the appearance of wrinkles.

The invention claimed is:

1. An active ingredient intended for use in a composition for skin application, wherein the active ingredient is a hydrolysate of *Eucheuma cottonii* comprising linear galactans, wherein less than 1% by weight of the linear galactans are sulfated, obtained by a process comprising the steps of: solubilizing *Eucheuma cottonii* powder in an aqueous solution, hydrolyzing carbohydrates in said solution, separating soluble and insoluble phases obtained after hydrolyzing, and recovering the soluble phase, filtering the soluble phase and recovering, as an active fraction, the filtrate containing the linear galactans, concentrating the active fraction, filtering the concentrated active fraction, and sterilizing filtering the filtered concentrated fraction.

2. The active ingredient according to claim 1, wherein the active ingredient comprises carbohydrates for at least 45% by weight of dry material.

3. The active ingredient according to claim 1, wherein less than 1% by weight of carbohydrates present in the active ingredient are sulfated carbohydrates.

4. The active ingredient according to claim 1, wherein the active ingredient is a non-viscous liquid product.

5. The active ingredient according to claim 1, wherein the active ingredient has at least one of:
 a level of dry materials of between 30 and 100 g/l, or
 a carbohydrate content of between 19 and 71 g/l.

6. The active ingredient according to claim 1, wherein the active ingredient has at least one of:
 a level of dry materials of between 47 and 65 g/l, or
 a carbohydrate content of between 31 and 46 g/l.

7. The active ingredient according to claim 1, wherein the linear galactans have a degree of polymerization of between 6 and 18.

8. A method of protecting the telosome and telomeres of the cells of the skin, comprising applying to the skin of a subject in need thereof an effective amount of an active ingredient according to claim 1 or a composition comprising said active ingredient.

9. The method according to claim 8, wherein protecting the telosome and telomeres of the cells of the skin comprises preserving POT1 and TPP1 expression and/or limiting a shortening of the telomeres of the cells of the skin.

10. The method according to claim 8, wherein protecting the telosome and telomeres of the cells of the skin comprises maintaining replicative potential of the cells of the skin.

11. The method according to claim 9, wherein protecting the telosome and telomeres of the cells of the skin comprises combating an aging of the skin.

12. The method according to claim 9, wherein the protecting the telosome and telomeres of the cells of the skin comprises combating an appearance of wrinkles.

13. A cosmetic composition for topical application, wherein it comprises the active ingredient according to claim 1 and the active ingredient has between 0.01 and 3% by weight of the composition.

14. A cosmetic method for care of the human skin, intended to combat effects of age on the skin, comprising the topical application on the skin of a composition containing non-sulfated linear galactans obtained from *Eucheuma cottonii* or the composition according to claim 13.

15. A cosmetic method for care of the human skin, intended to combat appearance of wrinkles, comprising the topical application on the skin of a composition of a composition containing non-sulfated linear galactans obtained from *Eucheuma cottonii* or from the composition according to claim 13.

* * * * *